United States Patent
Jassim et al.

(10) Patent No.: US 10,335,438 B2
(45) Date of Patent: Jul. 2, 2019

(54) CAMELID COMPOUND(S), COMPOSITION(S) AND METHOD(S)

(71) Applicant: APPLIED BIO RESEARCH INC., Windsor (CA)

(72) Inventors: Sabah Abdul Amer Jassim, Windsor (CA); Atheer Abdulrazzaq Abdulrazeez Al Doori, Baghdad (IQ); Richard George Limoges, Windsor (CA)

( * ) Notice: Subject to any disclaimer, the term of this patent is extended or adjusted under 35 U.S.C. 154(b) by 0 days.

(21) Appl. No.: 14/773,382

(22) PCT Filed: Dec. 27, 2013

(86) PCT No.: PCT/IB2013/061374
§ 371 (c)(1),
(2) Date: Sep. 7, 2015

(87) PCT Pub. No.: WO2014/135934
PCT Pub. Date: Sep. 12, 2014

(65) Prior Publication Data
US 2016/0022741 A1    Jan. 28, 2016

Related U.S. Application Data

(60) Provisional application No. 61/774,206, filed on Mar. 7, 2013.

(51) Int. Cl.
| | | |
|---|---|---|
| A61K 35/35 | (2015.01) | |
| A61Q 19/08 | (2006.01) | |
| A61Q 19/00 | (2006.01) | |
| A61K 8/67 | (2006.01) | |
| A61K 8/36 | (2006.01) | |
| A61Q 17/04 | (2006.01) | |
| A61K 8/92 | (2006.01) | |

(52) U.S. Cl.
CPC ........... *A61K 35/35* (2013.01); *A61K 8/361* (2013.01); *A61K 8/678* (2013.01); *A61K 8/925* (2013.01); *A61Q 17/04* (2013.01); *A61Q 19/007* (2013.01); *A61Q 19/08* (2013.01)

(58) Field of Classification Search
None
See application file for complete search history.

(56) References Cited

U.S. PATENT DOCUMENTS

| | | | | |
|---|---|---|---|---|
| 2007/0154443 A1* | 7/2007 | Kalejman | ............... | A61K 8/986 424/74 |
| 2014/0178487 A1* | 6/2014 | Nili | ........................ | A61K 35/35 424/522 |

FOREIGN PATENT DOCUMENTS

| | | |
|---|---|---|
| DE | 102010016134 A1 | 9/2011 |
| WO | 2005023208 A1 | 3/2005 |

OTHER PUBLICATIONS

Konuspayeva et al.; Dairy Sci. Technol. 88 (2008); pp. 327-340.*
Haasmann, Stephan Otto; "Analytical Characterizaation of Camel Meat and Milk Fat"; Doctoral Thesis Submission; Dec. 1998.*
Goldstein et al.; Am. Fam. Physician; 2001; 63: 1359-68, 1374.*
First Degree Burn definition and symptoms (www.urmc.rochester.edu/encyclopedia/content.aspx?ContentTypeID=90&ContentID=P01744)—downloaded Jan. 24, 2019.*
Second Degree Burn definition and symptoms (www.urmc.rochester.edu/encyclopedia/content.aspx?ContentTypeID=90&ContentID=P01757)—downloaded Jan. 24, 2019.*

* cited by examiner

*Primary Examiner* — Jeffrey T. Palenik
(74) *Attorney, Agent, or Firm* — Henry J Cittone; Cittone Demers & Arneri LLP

(57) ABSTRACT

Described herein are compounds, compositions and methods for the treatment of a subject having cancer, skin conditions, blood flow and/or growth failure. In one aspect of the present invention, there is provided compositions and methods for treating a subject having cancer, skin conditions, blood flow and/or growth failure, comprising fat derived from a camel. There are also described sunscreen and photoprotective compounds, compositions and methods, comprising fat derived from a camel.

5 Claims, No Drawings

CAMELID COMPOUND(S), COMPOSITION(S) AND METHOD(S)

CROSS-REFERENCE TO RELATED APPLICATIONS

This application is the U.S. national stage of PCT International Patent Application No. PCT/IB2013/061374, filed Dec. 27, 2013, which claims priority to U.S. Provisional Patent Application No. 61/774,206, filed Mar. 7, 2013, the disclosures of each of which are hereby incorporated by reference in their entirety.

FIELD OF THE INVENTION

The field of the invention generally relates to compounds, compositions and methods for the treatment of cancer, skin conditions, blood flow and/or growth failure. More specifically, the invention relates to compounds, compositions and methods derived from camel fat for the treatment of cancer, skin conditions, blood flow and/or growth failure.

BACKGROUND OF THE INVENTION

Ultraviolet Radiation Damage, Cancer, Burns, Age Spots

Ultraviolet (UV) radiation is carcinogenic and a principal cause of skin cancers. Exposure to UV radiation may come from a variety of sources, including from the sun, tanning bed use, etc.

UV's genotoxic potential is linked to its ability to provoke direct DNA damage. The depth of transmission of UV light is dependent on the wavelength: UVC only penetrates the superficial layer of the skin; UVB penetrates the basal level of the epidermis and UVA penetrates the dermis level. Of the three categories of solar UV radiation, typically UVA and UVB are of greatest concern to humans, especially as depletion of the ozone layer causes higher levels of this radiation to reach the planet's surface (Clancy 2008).

The skin is made up of a variety of cell types, including squamous cells, basal cells and melanocytes. Cancers of the skin are classified by the cell type they affect: squamous cell carcinoma (SCC), basal cell carcinoma (BCC) and melanoma, respectively.

Sunscreens prevent the direct DNA damage that causes sunburn by blocking UVB. As such, most of these products contain a sun protection factor (SPF) rating that indicates how well they block UVB as a measure of their effectiveness (SPF is therefore also called UVB-PF, for UVB protection factor) (Stephens et al. 2011). This rating offers no data about protection against UVA exposure, which does not lead to sunburn but is still harmful since it causes indirect UV DNA damage and is also considered carcinogenic. Some sunscreen lotions now include compounds such as titanium dioxide, which helps protect against UVA rays. Other UVA blocking compounds found in sunscreens include zinc oxide and avobenzone.

The active ingredients in sunscreens are either chemical or mineral based. The principal ingredients in sunscreens are usually aromatic molecules conjugated with carbonyl groups. This general structure allows the molecule to absorb high-energy ultraviolet rays and release the energy as lower-energy rays, thereby preventing the skin-damaging ultraviolet rays from reaching the skin. So, upon exposure to UV light, most of the ingredients (with the notable exception of avobenzone) do not undergo significant chemical change, allowing these ingredients to retain the UV-absorbing potency without significant photodegradation. A chemical stabilizer is included in some sunscreens containing avobenzone to slow its breakdown—examples include formulations containing Helioplex and AvoTriplex. The stability of avobenzone can also be improved by bemotrizinol (Chatelain and Gabard 2001), octocrylene; and various other photostabilisers.

Olive oil was often used as the source of free fatty acid due to its high oleic acid and squalene content, which can help protect skin against free radical-generated damage induced by UV light (Ching 2008). Other natural and organic ingredients that may be used in a natural sunscreen recipe include sesame, coconut, avocado or Emu oils and Aloe vera or shea butter as they can absorb much of the sun's rays Alopecia Alopecia, hair thinning and baldness refer to a partial or complete absence of hair and is found in both men and women. Although typically most noticeable on the scalp of an individual, it can occur anywhere on the body where hair grows.

An individual with alopecia may suffer from loss or lowering of self-esteem. Alopecia is a disease that affects the hair follicles, which are part of the skin from which hairs grow. The disease is an autoimmune disease in which the immune system attacks the hair follicles.

A variety of approaches are used to mask alopecia, such as wigs, weaves, hats, scarves, surgical implants, etc., which underscores the issues of self-esteem and methods to reduce or minimize the effects of alopecia. There is an unmet need for the treatment of alopecia.

Short Stature and/or Growth Failure

Growth is a fundamental aspect in the development of an organism and is regulated by a highly organized and complex system. Height is a multifactorial trait, influenced by both environmental and genetic factors. Developmental malformations concerning body height are common phenomena among many species. There is an unmet need in the treatment of short stature and/or growth failure.

Eczema

Eczema is a common problem that causes the skin to become inflamed. It is also known as dermatitis. Eczema or dermatitis comes in many forms, and is not one specific skin condition. Common symptoms are:

Itching. Sometimes intense with damage to the skin during eczema often due to scratching.

Scaling. The surface of the skin can flake off, giving the skin a rough, scaly appearance.

Redness. The affected skin may bleed and appear blotchy.

Fluid-filled blisters. These can ooze and form crusts.

Cracking. Severely affected skin may develop painful, deep cracks, also called fissures.

Depending on the cause, eczema may flare up and cause severe symptoms, but it can also become a chronic problem with less intense symptoms.

Medical research continues to show that the most effective treatment plan for eczema—regardless of type—involves using a combination of therapies to treat the skin and making lifestyle changes to control flare-ups. Doing so tends to increase effectiveness and reduce side effects from medications.

Leathery and Dry Skin on Elbows

This fairly common skin pigmentation disorder often occurs as we lean on our elbows for extended and repeated periods of time. The most notable sign is dark patches of skin at the elbows with a thick, velvety texture.

Age Spots

Age spots, also called liver spots, are flat brown patches on the skin that have darkened in color ("pigmented") after exposure to sunlight or ultraviolet light. They are commonly seen in people over the age of 40 on areas of skin that are frequently exposed to sunlight, such as the hands, shoulders, forearms, face and forehead. Age spots may look unattractive, but are painless and harmless, although their dark color can delay the diagnosis of some skin cancers.

Blood Flow

Blood flow is the continuous circulation of blood in the cardiovascular system to ensure the transportation of nutrients, hormones, oxygen, carbon dioxide, waste, etc to different body parts to maintain cell-level metabolism, pH regulation, temperature and osmotic pressure for the whole body and the protection from microbial and mechanical harms (Tortora and Derrickson, 2012).

Good blood circulation is essential to maintaining a healthy body. In order maintain a healthy body it is vital to have an adequate and developing blood supply to various tissues in order to induce cell activity for treating wrinkles, looking young, treating burns, infections, hair growth, wounds healing, musculoskeletal regeneration, especially in fracture healing, cartilage regeneration, muscle repair, etc.

Lessened or decreased blood flow in tissues can be due to a number of reasons.

Anemia (also spelled as "anaemia" and "anæmia") is a decrease in number of red blood cells (RBCs) or less than the normal quantity of hemoglobin in the blood. Because hemoglobin (found inside RBCs) normally carries oxygen from the lungs to the capillaries, anemia leads to hypoxia (lack of oxygen) in organs. Since all human cells depend on oxygen for survival, varying degrees of anemia can have a wide range of clinical consequences.

Hypoxia (also known as hypoxiation) is a condition in which the body or a region of the body is deprived of adequate oxygen supply. Hypoxia may be classified as either generalized, affecting the whole body, or local, affecting a region of the body. Although hypoxia is often a pathological condition, variations in arterial oxygen concentrations can be part of the normal physiology, for example, during strenuous physical exercise.

Heart failure (HF), often called congestive heart failure (CHF) or congestive cardiac failure (CCF), occurs when the heart is unable to provide sufficient pump action to maintain blood flow to meet the needs of the body. Heart failure can cause a number of symptoms including shortness of breath, leg swelling, and exercise intolerance.

Ischemia (also spelled as ischaemia or ischaemia) is a restriction in blood supply to tissues, causing a shortage of oxygen and glucose needed for cellular metabolism (to keep tissue alive). Ischemia is generally caused by problems with blood vessels, with resultant damage to or dysfunction of tissue. It also means local anemia in a given part of a body sometimes resulting from congestion (such as vasoconstriction, thrombosis or embolism).

Atherosclerosis (or arteriosclerotic vascular disease) is a condition where the arteries become narrowed and hardened due to an excessive build up of plaque around the artery wall. The disease disrupts the flow of blood around the body, posing serious cardiovascular complications.

Venous thrombosis is poor blood circulation due to veins becoming inflamed, often as a result of blood clots becoming lodged in the veins. This can lead to tenderness, skin discoloration and swelling in the area where the vein is being affected.

Polycythaemia rubra vera, is a condition in which there is an abnormally high number of red blood cells in the blood or an abnormally high number of platelets and white blood cells. Because of the extra number of blood cells circulating, the blood becomes thicker or more sludgy than normal.

Blood rheology factor that influences local tissue perfusion due to viscosity of blood depends on several factors, including hematocrit, red blood cell deformability and aggregation, and leukocyte activation.

Stroke occurs when the brain is deprived of the oxygen it needs due to an interruption of its blood supply. Without oxygen brain cells die. The oxygen deprived area of brain tissue is called an infarct.

Peripheral vascular disease (PVD) refers to diseases of the blood vessels (arteries and veins) located outside the heart and brain.

Gangrene is reduced blood supply to the affected tissues, which results in cell death.

Inadequate exercise can also lead to poor blood circulation. Other causative factors include spending a great deal of time driving or in airplane travel, or a neutral position such that blood in the pelvis and legs can become stagnant, which can lead to poor circulation and blood pooling.

Combining a lack of exercise with poor diet and smoking can also increase the risk of developing a dangerous blood circulation condition.

Tight fitting clothing can decrease blood circulation, most notably in the pelvic region. Control-top pantyhose, tight shirts or skinny jeans are just a few examples of clothing that can contribute to this issue.

Stress can also lead to poor circulation, most notably in the hands. Stress leads to knots in the muscles in the shoulders and neck, which can restrict blood flow to the heart and other major organs.

Frostbite is the medical condition where localized damage is caused to skin and other tissues due to freezing. Frostbite is most likely to happen in body parts farthest from the heart and those with large exposed areas. The initial stages of frostbite are sometimes called "frost nip".

Aging will cause some changes in the heart and blood vessels.

Skin Tightening and Ant-Wrinkling Properties

A wrinkle, also known as a rhytide, is a fold, ridge or crease in the skin. Skin wrinkles typically appear as a result of aging processes such as glycation, habitual sleeping positions, loss of body mass, or temporarily, as the result of prolonged immersion in water. Age wrinkling in the skin is promoted by habitual facial expressions, aging, sun damage, smoking, poor hydration, excess alcohol consumption and various other factors.

Athlete's Foot

Athlete's foot also known as ringworm of the foot and tinea pedis is a fungal infection of the skin that causes scaling, flaking, and itching in affected areas. Although the condition typically affects the feet, it can spread to other areas of the body, including the groin. About 70% of the population in the world is believed to experience a cutaneous mycotic infection at some point in their lives. Athlete's foot, the most prevalent mycotic infection worldwide, is caused by a Dermatophytes mold the *Trichophyton* sp.

Camel Fat

Fat in a camel is not stored subcutaneously over an extensive area of the camel, as with humans and most animals that store their fat mixed in with muscle tissue or in a layer beneath the skin. Rather, it is stored in the hump on the back of the animal. In a healthy, well-fed camel, the hump can weigh as much as 35 kilograms. Camel fat is also present in the milk, blood, meat and bones of the camel. Advantageously, the fat contained in the hump can be obtained via liposuction without killing the camel, leaving the camel to survive and generate more fat. The fat from the hump also contains fibrous proteinaceous connective tissue, which prevents the melting of the fat and may have positive medicinal activities.

In *Camelus dromedaries* the main fatty acid composition of camel hump fat is palmitic acid C16:0 (mole 33.8%), stearic acid C18:0 (mole 25.9%); oleic acid C18:1 (mole 18.1%); and myristic acid C14:0 (mile 6.3%) (Haasmann 1998). The saturated fatty acids are 74.2%, clearly demonstrating that camel hump fat contains a higher proportion of saturated fatty acids than fats from other sources, as previously reported (Haasmann 1998). This partially accounts for the fact that camel hump fat has a higher melting point than, for example, porcine fat (Haasmann 1998).

The component acids of camel fat of *Camelus bactrianus* were reported (Gunstone and Russell 1954). They found that camel fats are more saturated than the average sheep or ox tallow and this is reflected mainly in the increased content of stearic acid and decreased amount of oleic acid.

SUMMARY OF THE INVENTION

An object of the present invention is to provide compounds, compositions and methods for the treatment of a subject having conditions such as cancer, conditions of the skin, growth failure, diminished blood flow, or conditions associated with exposure to radiation.

In one aspect of the present invention, there is provided a composition for the treatment of a subject having cancer, comprising fat derived from the hump of a camel. In one example, said cancer is melanoma.

In one aspect of the present invention, there is provided a composition for the treatment of a subject having one of more of the following disorders: a) alopecia; b) short stature and/or growth failure; c) eczema; d) atopic dermatitis; e) seborrhoeic dermatitis; f) leathery and dry skin on elbows; g) age spots; h) lessened blood flow in tissues; i) loosened skin and wrinkles; or j) Athlete's Foot, comprising fat derived from the hump of a camel.

In one aspect of the present invention, there is provided a composition for the treatment of a subject having, suspected of having, or at risk of having a condition associated with exposure to radiation comprising fat derived from the hump of a camel. In one example, said radiation is ultraviolet radiation.

In one aspect of the present invention, there is provided a composition for photoprotection, comprising fat derived from the hump of a camel.

In one embodiment, the fat derived from the hump of a camel comprises at least one of palmitic acid, stearic acid, oleic acid, myristic acid, omega 3, 6, 9 or Vitamin E.

In another embodiment, the fat derived from the hump of a camel is prepared by: (i) heating a portion of fat from a camel hump; and (ii) removing impurities from said heated camel fat. In one example, the portion of camel fat is heated at about 60° C. for about 45 minutes. In another example, the portion of camel fat is heated at about 100° C. for about 20 minutes.

In one aspect of the present invention, there is provided a method to treat a subject having cancer, suspected of having cancer, or at risk of developing cancer comprising administering fat derived from the hump of a camel. In one example, the said cancer is melanoma.

In one aspect of the present invention, there is provided a method to treat a subject having one of more of the following disorders: a) alopecia; b) short stature and/or growth failure; c) eczema; d) atopic dermatitis; e) seborrhoeic dermatitis; f) leathery and dry skin on elbows; g) age spots; h) lessened blood flow in tissues; i) loosened skin and wrinkles; or j) Athlete's Foot, comprising administering fat derived from the hump of a camel.

In one aspect of the present invention, there is provided a method to treat a subject having, suspected of having, or at risk of having a condition associated with exposure to radiation, comprising administering fat derived from the hump of a camel. In one example, the said radiation is ultraviolet radiation.

In one embodiment, the administration of the fat derived from the hump of the camel is topical administration.

In another embodiment, the fat derived from the hump of a camel comprises at least one of palmitic acid, stearic acid, oleic acid, myristic acid, omega 3, 6, 9 or Vitamin E.

In another embodiment, the fat derived from the hump of a camel is prepared by (i) heating a portion of fat from a camel hump and (ii) removing impurities from said heated camel fat. In one example, the portion of camel fat is heated at about 60° C. for about 45 minutes. In another example, the portion of camel fat is heated at about 100° C. for about 20 minutes.

In one aspect of the present invention, a method is provided for preparing a sunscreen composition, a photoprotective composition, or a cancer therapeutic composition, comprising: (i) heating a portion of fat from a camel hump, (ii) removing impurities from said heated camel fat. In one example, the portion of camel fat is heated at about 60° C. for about 45 minutes. In another example, the portion of camel fat is heated at about 100° C. for about 20 minutes.

DETAILED DESCRIPTION

In the following description, the term "subject" (or "patient") as used herein, refers to any mammal or non-mammal that would benefit from treatment. In certain examples a subject or patient includes, but is not limited to, humans, farm animals (such as cows, sheep, pigs and the like), companion animals (such as cats, dogs, horses and the like), non-human primates, and rodents (such as mice, rats and the like). In a specific example, the subject is a human. The term "impurities" as used herein, refers to solid content in a portion of melted camel hump fat, which includes, but is not limited to, blood products, debris and pollutants.

Ultraviolet Radiation, Cancer, Burns, Age Spots

As will be described in more detail below, one aspect of the present invention relates to compounds, compositions and methods for the treatment of a subject with a condition associated with exposure to radiation.

In one aspect, there is provided sunscreen and photoprotective compositions and methods for the treatment of a subject, associated with the subject's exposure to UV radiation.

Also as will be described below, the present invention also relates to compositions and methods for the treatment of a subject at risk of developing cancer, having cancer, or suspected of having cancer, said cancer associated with the subject's exposure to UV radiation.

Thus, in accordance with one aspect of the present invention, there is provided sunscreen and photoprotective compositions and methods.

The sunscreen compositions and methods are useful in protecting the skin of a subject from UV radiation, and for example, sunburn due to UV radiation.

The photoprotective compositions and methods are useful for the treatment or prevention of cell damage from UV radiation, and for example, skin damage and injury due to UV radiation.

The term "skin damage and injury" due to UV radiation, includes, but is not limited to, UV-induced edema, erythema or thickening of the skin. Also included is sactinic keratoses, aging, discolorations, photokeratoconjunctivitis, photoageing, age spots (liver spots), moles and freckles, cataracts and other eye damage and diseases, retinal injury, wrinkles, swelling and blisters, skin redness, peeling and itching, rosacea, lupus erythematosus, hyperhidrosis, acute and chronic health effects, immune suppression.

In accordance with another aspect of the present invention, there is provided compositions and methods for the treatment of a subject at risk of developing cancer, having cancer, or suspected of having cancer, said cancer associated with a patient's exposure to UV radiation, comprising: administering to said subject a therapeutic composition. In one example, said therapeutic composition comprises fat derived from a member of the Camelidae family.

Radiation sources in addition to UV radiation are also contemplated, and include, but are not limited to X-ray, microwave, and nuclear radiation.

The term "cancer" as used herein, refers to or describes the physiological condition in a mammal that is typically characterized by unregulated cell growth. Cancers may be solid or non-solid cancers. Cancers may be a primary cancer and/or metastatic cancer. Cancers include, but are not limited to, a solid cancer, a non-solid cancer, a primary cancer, a metastatic cancer.

In a specific example, the cancer is a result of UV exposure. In a more specific example, the cancer is squamous cell carcinoma (SCC), basal cell carcinoma (BCC), or melanoma. In another example, the cancer is leukemia, thyroid cancer, female breast cancer, bone cancer, lung cancer, or cutaneous T cell lymphoma.

The term "treating", "treatment", or "lessening the severity", refers to any reduction using the methods, compounds and composition disclosed herein. Non-limiting example of "treatment" include, enhancement of patient survival, halting disease progression, delay in disease progression, diminishment of pain, delay in disease spread to alternate sites, organs or systems. Treatment also encompasses lessening of severity, amelioration or palliation of the disease state, and remission or improved prognosis. Treatment may comprise a reduction in the amount/dosage of radiotherapy and/or chemotherapy otherwise required to treat a subject, thereby resulting in a reduction of normal tissue damage. It is to be understood that any clinically beneficial effect that arises from the methods, compounds, compositions and methods disclosed herein, is considered to be encompassed by the invention.

Additional conditions which are suitable for treatment using the compounds and compositions of the present invention, include, but are not limited to cosmetic application, anti-aging, immunosuppressive conditions, and the like.

In a specific example, treatment is carried out in vivo.

In a another example, treatment is carried out in vitro, including but not limited to, in test tube, in cultured cells (both adherent cells and non-adherent cells), and the like.

In another example, treatment is carried out ex vivo, including but not limited to, in test tube, in cultured cells (both adherent cells and non-adherent cells), and the like.

In the case of sunscreen and photoprotective uses, the compounds and compositions of the present invention may also include one or more additional cosmetic compositions. Non limiting examples of cosmetic composition include vegetable oils; esters such as octyl palpitate, $C_{12-15}$ alkyl benzoate, isopropyl myristate and isopropyl palpitate; ethers such as dicapryl ether and dimethyl isosorbide; alcohols such as ethanol and isopropanol; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; polyols such as propylene glycol, ethoxydiglycol, glycerin, butylene glycol, pentylene glycol and hexylene glycol; an elastomer, or any combinations thereof.

Additionally, in the case of sunscreen and photoprotective uses, the compounds and compositions of the present invention may also include one or more additional composition, including, but not limited to, anesthetics, anti-allergenics, antifungals, antimicrobials, anti-acne, anti-inflammatories, antiseptics, chelating agents, botanical extracts, colorants, depigmenting agents, emollients, exfollients, film formers, fragrances, humectants, insect repellents, poison ivy, oak and sumac protestants, lubricants, moisturizers, pharmaceutical agents, preservatives, skin protestants, skin penetration enhancers, stabilizers, surfactants, thickeners, viscosity modifiers, vitamins, or any combinations thereof.

In the case of the treatment of cancer in a subject, the compositions comprising agents disclosed herein may be used in the methods described herein in combination with standard chemotherapeutic regimes or in conjunction with radiotherapy. Treatment of various cancers, such as, for example, melanoma, are well known to the skilled worker.

In one example, a composition of the present invention is applied to the skin of a subject prior to exposure to UV radiation. In another example, a composition of the present invention is applied to the skin of a subject subsequent to exposure to UV radiation. In another example, a composition of the present invention is applied to the skin of a subject during exposure to UV radiation. In another example, a composition of the present invention is applied to the skin of a subject prior to, and/or subsequent to, and/or during, exposure to UV radiation.

In one example, there is provided a method of preparing a sunscreen composition, a photoprotective composition, or a cancer therapeutic composition, comprising isolating camelid fatty acids present in camel hump fat, for example palmitic acid, stearic acid, oleic acid, myristic acid, omega 3, 6, 9 or Vitamin E, either in combination or individually, for treating a subject with a condition associated with exposure to radiation, cancer cells, age spots and skin burns.

Alopecia

In accordance with an another aspect of the present invention, there is provided compounds, compositions and methods for the treatment of a subject at risk of developing alopecia, having alopecia, or suspected of having alopecia, comprising: administering to said subject a therapeutic compound or composition. In one example, said therapeutic composition comprises fat derived from a member of the Camelidae family.

The term "alopecia" as used herein, refers to hair loss, any degree of hair thinning, or baldness.

The term "hair", typically refers to the hair on a human, whereas the term "fur" typically refers non-human mammalian hair. As used herein, the terms "hair" and "fur" will be used interchangeably, and the term "hair" shall be taken to include "fur", and vice versa. The term "hair" shall also be taken to include hair on any part of a mammalian body, including, but not limited to, the head, arms, legs, chest, back, genitals, eyebrow, edge of the eyelid (e.g., eyelashes), armpit, or other body part(s) or location(s).

Hair has two distinct structures: the follicle, which resides in the skin, and the shaft, which is what is visible above the scalp.

Hair growth may be divided into separate stages of growth and shedding, namely, anagen, catagen, and telogen.

Anagen is an active phase of the hair, in which cells in the root of the hair are dividing rapidly and new hair is formed. Catagen is a transitional stage in which hair growth stops and hair is anchored. Telogen is a resting phase in which the folice is at rest.

Hair loss or hair thinning includes any condition that results in a reduced ability to replace shed hairs or that results in enhanced shedding without their concomitant or subsequent replacement. A deregulated hair cycle (or the biochemica components that constitute the hair cycle), for example, may lead to accelerated hair loss, which may be temporary or permanent.

Alopecia may result from hereditary causes and non-hereditary causes, or both.

Alopecia, irrespective of the cause, is often associated with lowered self-esteem.

As used herein, the term "treat" or "treating" or "treatment", in the context of alopecia, refer to use of a therapeutically effective amount of a pre-existing condition, or prophylactically effective amount or preventative measures, wherein the aim is to prevent, ameliorate, reduce or slow down (lessen) hair thinning, hair loss or alopecia. A mammal in need of treatment of alopecia may already have the condition, or may be prone to have the condition or may be in whom the condition is to be prevented. Treatment may also comprise a reduction in the amount/dosage of an existing alopecia therapy otherwise required to treat a subject. A mammal in need of prevention may be prone to develop the condition.

The active compounds and compositions are for administration to an individual in a "prophylactically effective amount" or a "therapeutically effective amount" (as the case may be, although prophylaxis may be considered therapy), this being sufficient to show benefit to the individual in the context of alopecia herein. For example, therapeutically effective amount refers to an amount of the composition capable of reducing hair thinning, hair loss or alopecia in a mammal to a level that is beneficial to treat or prevent hair thinning, hair loss or alopecia. The actual amount administered, and rate and time-course of administration, will depend on the nature and severity of the alopecia being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners.

The term "ameliorate" or "amelioration", in the context of alopecia herein, refers to a decrease, reduction or elimination of a condition, disease, disorder, or phenotype, including an abnormality or symptom.

In one embodiment the present invention relates to a topical cream or an emulsion for the treatment of alopecia in a subject.

In one embodiment, alopecia treated by a composition of the present invention is caused by one or more factors selected from hereditary, age, environmental effects, chemotherapy, radiotherapy, radiation exposure, childbirth, fertility drugs, surgery, poisoning, stress, iron deficiency, infection (including viral, bacterial, fungal or mycotic infections), autoimmune disorders, lupus, tumours, skin outgrowths, hypothyroidism, hyperthyroidism, stress, malnutrition, hormonal disorder, or any agent(s) or disorder(s) that may induce necrosis or apoptosis of the hair follicle, or prevent the follicle to enter anagen.

In another embodiment, alopecia treated by a composition of the present invention is one or more of hereditary alopecia or non-hereditary alopecia.

In another embodiment, alopecia treated by a composition of the present invention is one or more of alopecia comprises androgenic alopecia, alopecia areata, alopecia totalis, or alopecia universalis, or telogen effluvium.

In yet another embodiment a composition of the present invention discloses a topical composition for stimulating hair growth, or preventing hair loss.

In specific examples, a therapeutically effective amount of a composition of the present invention is used in the treatment of alopecia in a subject.

The compounds and compositions of the present invention for the treatment of alopecia may be formulated in any form used in the pharmaceutical or cosmetic field, desirably suitable for topical administration. For example, the composition may be a hair-growing product, hair or scalp cosmetic (e.g. shampoo, hair conditioner, scalp lotion, scalp cream, hair tonic, etc.), skincare product (e.g. lotion, cream, face cream, face lotion, milk, pack, liquid facial wash, soap, etc.), body care product (e.g. body cream, body lotion, soap, liquid wash, bath additive, etc.), UV protective agent (e.g. sun block, sunscreen lotion, tanning oil, etc.), or cosmetic (e.g. eyeliner, eyebrow pencil, cream, lotion, etc).

The compounds and compositions for the present invention for the treatment of alopecia may also include existing therapies for alopecia including one or more of minoxidil, spironolactone, cyproterone acetate, ketoconazole, flutamide, finasteride (Propecia), progesterone, estrogen, prostaglandin analogs such as travoprost and voprostol, hair transplantion, or treatment with laser.

Short Stature and Growth Failure

In accordance with an another aspect of the present invention, there is provided compounds, compositions and methods for the treatment of a subject at risk of developing short stature and/or growth failure, or suspected of having short stature and/or growth failure, comprising: administering to said subject a therapeutic compound or composition. In one example, said therapeutic composition comprises fat derived from a member of the Camelidae family.

Short stature is typically considered to be a height more than two standard deviations below the mean (or below the 2.5 percentile) for a given age and gender, as compared to a well nourished, genetically relevant, population. Short stature is often a normal variant, however, short stature may be a sign of a wide variety of pathologic conditions or inherited disorders.

Causes of short stature include familial short stature, or constitutional delay of growth and development (i.e., "late bloomers"), and chronic disease (including malnutrition and genetic disorders).

While most cases of short stature have familial short stature or constitutional delay of growth and development, other causes include, but are not limited to, psychosocial deprivation, hyperphagic short stature syndrome, intrauterine growth restriction, etomaternal factors, prematurity, placental dysfunction, congenital, eg Russell-Silver syndrome, malnutrition, inflammatory bowel disease, coeliac disease, bowel obstruction, enzyme deficiencies, chronic bowel infection, chronic disease, cardiovascular disease, respiratory disease, haemoglobinopathies, kidney disease, acidosis, malignancy, neurological (eg hydrocephalus), skeletal dysplasias, chondrodysplasias, osteogenesis imperfecta, rickets, chromosomal abnormalities, Turner's syndrome, trisomy syndromes, endocrine, hypothyroidism, panhypopituitarism, Laron's syndrome, Cushing's syndrome, pseudohypothyroidism, growth hormone deficiency or insufficiency, metabolic mucopolysaccharidoses, glycogen storage disease, drugs, steroids, genetic mutations such as SHOX gene mutation(s).

When no clear cause of short stature has been identified in children with short stature and/or growth failure and with a prognosis of compromised adult height relative to target height, a widely used term is idiopathic short stature.

Children of short stature found to lack growth hormone typically are treated with growth hormone injections. Growth hormone injections are also typically used to treat Turner syndrome, Prader-Willi syndrome, chronic kidney failure, or idiopathic short stature (ISS).

Humatrope® (somatropin) is indicated in children who: do not make enough growth hormone on their own, have Turner syndrome, have idiopathic short stature, have SHOX deficiency.

Growth failure (also referred to as a growth velocity disorder) is a pathologic state of abnormally low growth rate over time indicative that a subject will not reach the genetically expected adult height. Short stature and growth failure often occur together, but not always.

As used herein, the term "treat" or "treating" or "treatment", in the context of short stature and/or growth failure, refer to use of a therapeutically effective amount of a pre-existing condition, or prophylactically effective amount or preventative measures, wherein the aim is to prevent, ameliorate, reduce or slow down (lessen) short stature and/or growth failure. A mammal in need of treatment of short stature and/or growth failure may already have the condition, or may be prone to have the condition or may be in whom the condition is to be prevented. Treatment may also comprise a reduction in the amount/dosage of an existing short stature and/or growth failure therapy otherwise required to treat a subject. A mammal in need of prevention may be prone to develop the condition.

The active compounds and compositions are for administration to an individual in a "prophylactically effective amount" or a "therapeutically effective amount" (as the case may be, although prophylaxis may be considered therapy), this being sufficient to show benefit to the individual in the context of short stature and/or growth failure. The actual amount administered, and rate and time-course of administration, will depend on the nature and severity of the short stature and/or growth failure being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners.

The term "ameliorate" or "amelioration", in the context of short stature and/or growth failure herein, refers to a decrease, reduction or elimination of a condition, disease, disorder, or phenotype, including an abnormality or symptom.

In one embodiment the present invention related to a topical cream or an emulsion for the treatment of short stature and/or growth failure in a subject.

In specific examples, a therapeutically effect amount of a composition of the present invention is used in the treatment of short stature and/or growth failure in a subject.

The term "therapeutically effective amount", in the context of short stature and/or growth failure, refers to an amount of the composition capable of reducing hair thinning, hair loss or alopecia in a mammal to a level that is beneficial to treat or prevent short stature and/or growth failure. A therapeutically effective amount may be determined empirically and in a routine manner in relation to treating short stature and/or growth failure.

The compounds and compositions of the present invention for the treatment of short stature and/or growth failure may be formulated in any form used in the pharmaceutical, quasi-drug, or cosmetic field, desirably suitable for topical administration. For example, the composition may be a hair or scalp cosmetic (e.g. shampoo, hair conditioner, scalp lotion, scalp cream, hair tonic, etc.), skincare product (e.g. lotion, cream, face cream, face lotion, milk, pack, liquid facial wash, soap, etc.), body care product (e.g. body cream, body lotion, soap, liquid wash, bath additive, etc.), UV protective agent (e.g. sun block, sunscreen lotion, tanning oil, etc.), or cosmetic (e.g. eyeliner, eyebrow pencil, cream, lotion, etc).

The compounds and compositions for the present invention for the treatment of short stature and/or growth failure may also include existing therapies for short stature and/or growth failure including growth hormone, Humatrope® (somatropin).

Eczema

In one embodiment the present invention relates to a topical cream or an emulsion for the treatment of eczema in a subject.

In specific examples, a therapeutically effective amount of a composition of the present invention is used in the treatment of eczema in a subject.

The term "therapeutically effective amount", in the context of eczema, refers to an amount of the composition capable of treating eczema in a human. A therapeutically effective amount may be determined empirically and in a routine manner in relation to treating eczema.

The compounds and compositions of the present invention for the treatment of eczema may be formulated in any form used in the pharmaceutical, quasi-drug, or cosmetic field, desirably suitable for topical administration. For example, the composition may be a scalp cosmetic (e.g. shampoo, scalp lotion, scalp cream, etc.), skincare product (e.g. lotion, cream, face cream, face lotion, milk, pack, liquid facial wash, soap, etc.), body care product (e.g. body cream, body lotion, soap, liquid wash, bath additive, etc.), eczema protective agent, or cosmetic (e.g. eyeliner, eyebrow pencil, cream, lotion, etc).

Compounds and Compositions

In one aspect of the present invention, the compounds and composition comprise fat derived from a member of the Camelidae family (in the order Artiodactyla and suborder Tylopoda). In a specific example, the fat is derived from a member of the genus *Camelus* within the family Camelidae. In a specific example, the fat is derived from a member of the species the *Camelus dromedaries* (a dromedary, the one-humped camels) within the family Camelidae. In a specific example, the fat is derived from a member of the species *Camelus bactrianus* (a bactrian camel, the two-humped camels) within the family Camelidae.

In another aspect of the invention, the composition comprises fat derived from Arabian sheep (fat-tailed type).

In another aspect of the invention, the composition comprises fat derived from a desert dwelling animal. Such a desert dwelling animal has typically lived for a number of generations in the desert (or under desert-like conditions). In yet another example, the composition comprises fat derived from a desert dwelling insect. Non-limiting examples of such animals and insects include roadrunners, black widow spider, meerkats, kangaroo rats, gerbils, rabbits, snakes, lizards, scorpions, coyotes, bobcats, bighorn sheep, barbary sheep, nubian ibex, addax, klipspringer, and baboon, include.

In one example, a composition of the present invention is prepared by obtaining fat from the hump of a camel, heating the fat at 60° C. for about 45 minutes, impurities are removed, and the resulting cream is stored at 10° C.

It will be appreciated that fat sources from the camel other than the hump are contemplated and include such non-limiting sources as camel blood, milk, urine, or the like.

Since the fat is the principal beneficial agent in camelid cream and is contained in camel milk and blood, the same properties and benefits can be derived from camel milk and camel blood, as it was observed that camel fat is transported through the blood.

Hence, a composition of the present invention is prepared by obtaining fat from the blood of a camel, heating the fat at 60° C. for about 45 minutes, impurities are removed, and the resulting cream is stored at 10° C.

In use, in one example, a composition of the present invention is applied topically to the skin of a subject at a concentration of about 1 g of cream per 1 $cm^2$ of skin. In another example, the concentration is greater that about 1 g of cream per 1 $cm^2$ of skin. In another example, the concentration is less than about 1 g of cream per 1 $cm^2$ of skin. In some examples, a composition is applied topically to the skin of a subject at a concentration of about 0.1 g to about 1 g cream per 1 $cm^2$ of skin.

In some examples, the compounds and compositions of the present invention are modified to further include, for example by conjugation to the camelid fat or fatty acids therein, one or more moieties that confer radiation protection from cosmic rays or electromagnetic radiation spectrum wavelengths $10^3$ to $10^{-12}$, e.g. radio or radioactivity or microwave or infrared or ultraviolet or x-rays or gamma rays, or UV light. Such moieties and method of conjugation are known to the skilled worker.

In another example, the compounds and/or compositions are provided in a pharmaceutically effective amount.

The term "pharmaceutically effective amount" as used herein refers to the amount of a drug or pharmaceutical agent that will elicit the biological or medical response of a tissue, system, animal or human that is being sought by a researcher or clinician. This amount can be a therapeutically effective amount.

The compounds and compositions are provided in a pharmaceutically acceptable form.

The term "pharmaceutically acceptable" as used herein includes compounds, materials, compositions, and/or dosage forms which are suitable for use in contact with the tissues of a subject (e.g. human) without excessive toxicity, irritation, allergic response, or other problem or complication, commensurate with a reasonable benefit/risk ratio. Each carrier, excipient, etc., is also considered "acceptable" in the sense of being compatible with the other.

The active compounds and compositions are for administration to an individual in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners.

The formulations may conveniently be presented in unit dosage form and may be prepared by any methods well known in the art of pharmacy. Such methods include the step of bringing the active compound into association with a carrier, which may constitute one or more accessory ingredients. In general, the formulations are prepared by uniformly and intimately bringing into association the active compound with liquid carriers or finely divided solid carriers or both, and then if necessary shaping the product.

A compound or composition of the present invention may be administered alone or in combination with other treatments, either simultaneously or sequentially, dependent upon the condition to be treated.

In one example, the administration is topical administration.

As used herein "topical administration" includes cream, ointment or spray applied to the skin. The composition can be made into any suitable product form, including by not limited to, an aerosol, balm, cream, gel, lotion, serum, mousse, patch, pomade, pump spray, roll-on, solution, stick or towelettes.

In other examples, the compound or composition is administered using eye drops.

In another example, the compound or composition is administered orally, for example in a capsule.

In some examples, the compounds and compositions of the present invention are produced as a nutritional supplement or functional food.

The compounds and compositions may also include one or more carriers. Examples of carriers include solutions, solvents, dispersion media, delay agents, emulsions and the like. For example, alcohols, glycols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxymethyl cellulose, polyvinyl pyrrolidine, etc. The pharmaceutical preparations can be sterilized, and, if desired, mixed with auxiliary agents, including lubricants, preservatives, stabilizers, wetting agents, emulsifiers, salts for influencing osmotic pressure, buffers and coloring. Solutions, suspensions, emulsions, or implants, can conveniently be provided for appropriate administration. The use of such carriers for pharmaceutical substances is well known in the art.

The formulations may be presented in unit-dose or multi-dose sealed containers.

Kits

Methods of the invention are conveniently practiced by providing the compounds and/or compositions used in such method in the form of a kit. Such a kit preferably contains the composition. Such a kit preferably contains instructions for the use thereof. Such a kit optionally contains additional compounds, compositions and/or instructions for the use thereof.

In one aspect of the present invention, there is provided a kit for the treatment of a subject having cancer, or suspected of having cancer, said cancer associated exposure to UV radiation, comprising: fat derived from the hump of a camel, and instructions of the use thereof. In another aspect, said kit further comprises, at least one chemotherapeutic agent to treat said cancer.

In one aspect of the present invention, there is provided a method for treatment or prevention of damage to a cell due to exposure to UV radiation, comprising: administering an effective amount of a sunscreen composition which comprises an effective amount of fat derived from the hump of a camel.

In one aspect of the present invention, there is provided a method for treatment or prevention of damage to a cell due to exposure to UV radiation, comprising: administering an effective amount of a photoprotective composition which comprises an effective amount of fat derived from the hump of a camel.

In one aspect of the present invention, there is provided a kit for the treatment of a subject having alopecia, or suspect of having alopecia, comprising: fat derived from the hump of a camel, and instructions of the use thereof. In another aspect, said kit further comprises, at least one agent to treat said alopecia.

In one aspect of the present invention, there is provided a kit for the treatment of a subject having short stature and/or growth failure, or suspect of having short stature and/or growth failure, comprising: fat derived from the hump of a camel, and instructions of the use thereof. In another aspect, said kit further comprises, at least one agent to treat said short stature and/or growth failure.

To gain a better understanding of the invention described herein, the following examples are set forth. It should be understood that these example are for illustrative purposes only. Therefore, they should not limit the scope of this invention in any way.

EXAMPLES

Example I

Treatment of Animals Exposed to UV Irradiation

Materials and Methods

Animals

Both male and female white BALB/c mice aged about 3-4 months weighing 24-31 grams were randomly divided into four groups of 10 animals and were housed in an animal facility and maintained throughout under standard conditions: 22±2° C., 50±10% relative humidity and 12 hour light/12 hour dark cycle. The mice were fed a standard diet and watered.

UV Irradiation

The experimental conditions were designed to simulate severe natural conditions, a solar simulator UV light type (F20 T8 GL 220-240 v UV CE) with a spectral range (360 nm-370 nm) corresponding to natural sunlight and environmentally relevant UVA doses were employed.

The dorsal shaved mice (2×3 cm in length) were clipped to keep animal position and exposed to doses of UVA radiation from about 15 cm from the source of light in a cabinet (75 cm long×50 cm width×75 cm high) for 4 hours per day for 3 months. During irradiation, the cages were regularly and systematically repositioned below the lights to reduce the variation in radiation intensity (±10%) in different positions and the temperature was stabilized with an electric fan.

A digital camera was used to monitor changes resulting from UV exposure and pictures were taken for this purpose.

Gross lesions were recorded and specimens of skin 1×1 cm were kept in 10% formalin and sent for histopathological examination to study the microscopic changes. Biosafety precautions were followed during the experiment due to the hazardous effect of UV light, such as wearing gloves, cups and masks along with an appropriate hood.

Preparation of Camelid Fat Cream

Fresh camel hump fat (28 Kg) from adult male dromedaries was obtained immediately after slaughtering. The camel hump fat was immediately stored at −80° C. For the experiments, about 500 gram of fat was defrosted to room temperature. Next it was placed in a lab beaker and heated to 60° C. for 45 minutes. The crude melted fat was cleaned of impurities using a food strainer (25 cm wire mesh sieve). The clear liquid fat was then collected in a clean sterile container and stored in a fridge at 10° C. to be ready for use. The end fat has a white color with a soft creamy texture that absorbs quickly on skin.

Histopathological Examination

All animals were sacrificed by inhalation of chloroform (Memmert, Germany) and postmortem examinations were completed.

Skin tissue was sampled and processed according to the following procedures.

All skin tissue samples were dissected to an equal size of 1×1 cm square. Each piece of tissue was immediately fixed in buffered 10% formalin saline (BDH, England). Subsequently, all the pieces were separately labeled and processed together, encased in a Shandon Elliot Histokinette tissue processor (Shandon Southern Products Ltd, Runcorn, UK).

Sets of histological sections were stained with hematoxylin stain (Thermo-Shandon, UK) and Eosin stain (Panreac Quimica, Spain). The histological evaluation was performed using an Olympus BX 40 light microscope.

Animal Treatment

In this research the animals were shaved and then divided into four groups with each group receiving treatments as follows:

1. Group A: Unprotected, daily exposure to UV light for 4 hours over 3 month period 2. Group B: Prior to the similar daily exposure to UV light for 4 hours over 3 months, each mouse was treated topically on the dorsal skin with about 1 gram of camelid fat cream to create a thin film of fat on the nude skin. The order of treatments was systematically rotated to ensure comparability of timing of fat applications, which were always completed within 5 minutes of the start of irradiation.

3. Group C: After unprotected daily exposure to UV light for 4 hours over 3 months, similar to Group A, camelid fat cream was applied topically each day for the subsequent 3 months.

4. Group D: Control group with neither camelid cream nor UV exposure.

Mid dorsal skin fold thickness was measured regularly during the three month test period in all 4 groups. Tumor appearance and growth was mapped and recorded for each mouse for tumors of diameter 1 mm or greater.

Results—I

Histopathological examination of the skin from the mice and analysis of tissue sections were performed.

Group A, following three months of radiation, animals had formation of cells with pyknotic nucleus and shrunken eosinophilic cytoplasm, (sunburn cells) in the epidermis of UV irradiated mice. There were also neutrophil and macrophage infiltration in subcutaneous tissue and around hair follicles, edema along and between muscle fibers and fibrin network deposition in adipose tissue. The sunburn cell production and focal inflammation were clearly visible. Erosion, necrosis of epidermal layer, focal hyperplasia of epithelial layer with hyper chromatic nuclei neutrophils and mononuclear cell infiltration in the dermis layer were also visible, as well as necrosis of the epithelial layer of hair follicle and sweat gland with neutrophils in their lumen in addition to edema and neutrophil infiltration between sweat gland and hair follicle. Signs of hemorrhage, congestion of blood vessels, edema, neutrophil infiltration, and cellular debris in the lumen of the hair follicle are present. Fibrous connective tissue proliferation and mononuclear cell infiltration in the adipose tissue were also clearly visible.

Group B (with camelid fat cream application prior to daily exposure) The protected skin of mice showed moderate mononuclear cell infiltration in the dermis layer and congestion of the blood vessel with normal epidermal layer. There was a normal structure of epidermal layer and limited mononuclear cell infiltration in the dermal layer, and focal aggregation of mononuclear cells around hair follicles which showed active fibroblast and normal structure of capacious gland.

Group C (camelid fat cream applied topically each day for the 3 months following exposure) showed clearly reduced necrosis and erosion of the epidermis, covered by cellular depression and inflammatory cell infiltration in dermis and subcutaneous layer. There was normal fibrous connective tissue proliferation, mononuclear cell infiltration between adipose tissue and muscular layer.

Group D (control), the histological section of skin of normal animal, not exposed to UV radiation, showed tissue with normal hair follicles.

The results of these in vivo experiments indicated that camelid fat cream prevented UV damage to the skin tissue in group B mice. The average skin protection rate of mice treated in group B with camelid fat cream was indistinguishable from healthy, normal mice in the control group D.

The histopathological examinations and daily observations also supported this finding.

The camelid cream had a noticeable healing effect on the skin of group C mice. The cells and tissue appear to be rejuvenated as compared to those from group A.

Based on the present results; it appears that camelid fat has an ability to repair UV damage.

Conclusions—I

Camel fat derived from the hump was used to produce a camelid fat cream. Surprisingly, the camelid fat cream was shown to shield UV radiation and to revive cells by repairing damage from UV, thus exhibiting cancer treatment properties.

The camel's hump fat cream appears to be highly effective in treating or preventing damage caused by UV and solar radiation including artificial sources of radiation, and provides protection from the effects of UVA/UVB irradiation including environmental damage to the skin or eyes; or allows longer UV radiation exposure by preventing damage; or prevents, treats, cures, or mitigates melanoma, other skin cancers or degenerative changes or damage to skin or eyes, non-melanoma skin cancers, cancer of the lip, degenerative changes in the cells, fibrous tissue and blood vessels of the skin, pterygium, cataracts and immunosuppression.

The camel's hump fat cream appears to be highly effective in treating or preventing damage caused by burns.

It appears that the major fatty acids present in camel hump fat, palmitic acid, stearic acid, oleic acid, myristic acid, omega 3, 6, 9 or Vitamin E, either in combination or individually, may have a significant effect on UV radiation, cancer cells, age spots and skin burns.

Example II

Comparison of Treatment of Animals with Sheep, Cow and Camel Fat Creams

Preparation of Cream from Fat-Tailed Sheep

Fat-tailed sheep (3.5 Kg) from adult male Awassi ram was obtained immediately after slaughtering. The fat was immediately stored at −80° C. In the experiments, about 500 gram of fat was defrosted to room temperature. The defrosted fat was then placed in a lab beaker and heated to 60° C. for 45 minutes. The crude melted fat was cleaned of impurities using a food strainer (25 cm wire mesh sieve). The clear liquid fat was then collected in a clean sterile container and stored in a fridge at 10° C. to for use. The cream from the fat-tailed sheep obtained has a whitish color with a soft creamy texture that absorbs less on the skin than that of camelid fat cream.

Preparation of Cream Cow Fat

Fresh fat (4.5 Kg) from adult male Friesian-Holstein was obtained immediately after slaughtering was immediately stored at −80° C. The fat from the animal was obtained from a position close to skin, on the animal's back. In the experiments, about 500 gram of fat was defrosted to room temperature. The defrosted fat was then placed in a lab beaker and heated to 60° C. for 45 minutes. The crude melted fat was cleaned of impurities using a food strainer (25 cm wire mesh sieve). The clear liquid fat was then collected in a clean sterile container and stored in a fridge at 10° C. to for use. The cream from the cow fat obtained has a yellowish creamy color with a soft creamy texture that absorbs much less on skin than that of camelid fat cream.

Histopathological Examination and Animal Treatment.

The histopathological examination and animal treatment for fat-tailed sheep and cows were similar to that as in Example I.

Results—II

With camelid fat cream application prior to daily exposure the protected skin of mice showed moderate mononuclear cell infiltration in the dermis layer and congestion of the blood vessel, with normal epidermal layer and a normal epidermal layer and limited mononuclear cell infiltration in the dermal layer. There were no clear lesions in the hair follicle.

With sheep fat cream application prior to daily exposure, the skin of mice in showed neutrophil infiltration around hair follicles and necrosis of muscle fibers, neutrophil infiltration with odema and congestion of blood vessels, hemorrhage and neutrophil infiltration within muscle fibers, neutrophil infiltration between hair follicles and vacuolation in the hair follicles, neutrophils infiltration in the dermis and in the dilated blood vessels, necrosis, neutrophil infiltration, erosions and sloughing of epidermal layer, destruction in the walls of hair follicles, odema and neutrophil infiltration.

With cow fat cream application prior to daily exposure the skin of mice showed congested and dilated blood vessels with neutrophils in their lumen, severe congestion of the blood vessels, with neutrophils in their lumen in the subcutaneous tissue, in addition to neutrophil infiltration, severe hypersensitivity of the hair follicles, marked neutrophil and mononuclear cell infiltration in the subcutaneous, proteinous material and neutrophils infiltrations in the necrotic epidermal layer.

Unprotected, daily exposure to UV light for 4 hours over 3 month period showed neutrophil infiltration within adipose tissue and inflammatory cells infiltration around sebaceous gland with calcification, congestion of dilated blood vessels with neutrophils in their lumen and odema in the interstitial tissue, abscess formation in subcutaneous tissue, neutrophil infiltration and fibrin deposition around blood vessels, necrotic areas surrounded by inflammatory cells and fibroblasts.

The histological section of skin of normal animal, not exposed to UV radiation, showed tissue with normal epidermal hair follicles and sebaceous gland with no lesion in adipose tissue and muscular layer of the skin.

The camel's hump fat cream was highly effective in treating or preventing skin damage on mice from UV radiation. In contrast, the sheep fat cream and cow fat cream did not protect mice's skin from radiation and in some cases the application of cow fat cream resulted in a large tumour (8 mm in diameter).

Example III

Treatment of Age Spots in Animals and Humans

Age spots, also called liver spots, are flat brown patches on the skin that have darkened in color ("pigmented") after exposure to sunlight or ultraviolet light. They are commonly seen in people over the age of 40 on areas of skin that are frequently exposed to sunlight, such as the hands, shoulders, forearms, face and forehead. Age spots may look unattractive, but are painless and harmless, although their dark color can delay the diagnosis of some skin cancers.

Methods—III

A female patient (41 years old) who had developed age spots on her hands was treated topically on both hands with about 1 gram of camelid fat cream to create a thin film of fat on the nude skin. The cream was applied at night and washed in the morning, repeated daily for 3 months.

After 3 month treatment the camelid fat cream has cleared over 80% of the age spots.

Further, a male patient (60 years old) who had developed age spots on his hands was treated topically on the right hand with about 1 gram of camelid fat cream to create a thin film of fat on the nude skin. The cream was applied day and night and washed in the morning, then applied repeatedly daily for 3 weeks. The left hand was not treated with the camelid cream as a control.

Another male patient (55 years old) with freckles or age spots covering both shoulders which appeared in his mid forties following repeated exposure to the sun. The cream was applied daily for two weeks resulting in a dramatic lightening of the freckles.

Results—III

After 3 weeks of treatment with camelid cream, age spots shrunk with very pale brown colour.

The skin of the second male patient after 3 weeks of treatment with the camelid cream, resulted in shrinking of the age spot, with the colour being reduced to a very pale brown colour.

From this result, camelid hump cream not only works as an anti-radiation but also for age spots.

Example IV

Treatment of Burns on Skin

In another example, the composition of the present invention is useful in the treatment of burns.

In this example a male patient (17 years old) with first-degree burn from boiling water over his hands and both anterior thighs was treated topically with camelid fat cream to create a thin film of fat on the nude skin. The cream was applied at night and in the morning for 2 weeks resulting in no infection, pain relief and re-growth of normal skin.

In another example, the camelid fat cream was used on a human skin burned by fire. The skin on the subject has healed within a few days.

Accordingly, the compositions of the present invention may be used in a variety of treatments, including kind treatments of burn obtained by fire, hot water, electricity, radiations, sunburn, and the like.

Example V

Treatment of Hairlessness

In the following example, the camelid fat cream was used to stimulate hair-growth in albino lab mice that showed stunted physical and reduced hair growth.

Before administering the topical treatment of camelid cream, the ten albino mice used as subjects in this example were characteristically normal at birth, but lacked hair growth and showed stunted physical development and unhealthy skin.

Methods—V

Ten albino lab mice that were characteristically normal size at birth were housed in a test facility under standard conditions: 22±2° C., 50±10% relative humidity. Mice were fed a standard diet and water.

All ten mice became stunted in growth shortly after birth and were approximately one-third normal size at 4 weeks of age.

At 4 weeks, although considered juvenile, the mice typically weighed only about 15 g. The length of the body from snout to the end of hip was about 6 cm, and the length of the tail from the end of the hip to full extent of the tail was about 6 cm.

Each mouse exhibited alopecia or hair loss, red skin, and appeared stressed. The mice were weak, unable to stand or move and exhibiting reduced immune function, though losses of appetite or diarrhoea were not found. Other signs of illness such as weight and fur loss were apparent.

At 4 weeks, the mice were divided into two groups, five mice in each group. One group received a daily topical treatment of camelid cream (as prepared in Example I, specifically the application of 1 gram of camelid fat cream to create a thin film of fat on 1 cm of nude skin with all body parts covered, 5 days a week for 4 weeks. The second group was left without treatment as a control. Both groups of mice were maintained in a conventional environment and fed the same unrestricted lab chow and tap water while housed in a test facility under standard conditions.

Results & Discussion—V

The mice that received the camelid cream once daily, five days per week for 4 weeks grew hair and gained weight from 15 g to 25 g, a 60% increase in weight and added 4 cm length to body from snout to the end of the tail within only 4 weeks. In comparison, the untreated mice that survived remained at a weight of about 15 g and overall size one third less than the accepted range within the subject community.

The treated mice all demonstrated hair growth. While not wishing to be bound by theory, it is postulated one or more compounds within the camelid cream induces hair growth by blocking (CRF) a stress-related hormone associated with hair loss.

In these mice, the hair follicles are dormant. The camelid compound appears to activate the follicles in tandem with improvements to health. The treatment not only reversed hair loss, it also prevented it when started prior to symptoms occurring. It has also restored normal pigmentation in the skin. Further, the treatment restores the original white colour of mice.

One mouse of the two surviving mice in the group that did not originally receive the treatment with camelid cream, received a daily topical treatment of camelid cream with all body parts covered following the initial experiment, for 5 days a week for the ensuing 3 weeks. After the first week of treatment, the mouse responded positively with hair starting to grow after only 3 days. Health and hair growth continued to improve each week. After 3 weeks, the mouse weighed 20 gm with normal length of body from snout to the end of hip (7 cm) and the length of the tail is 7 cm (normal adult weight and size) with thick complete fur cover.

In the experiments it was noted that the camelid cream is absorbed by the skin within 10 min of the topical treatment. Also, the treated mice in the experiments were licking the camelid cream from the body of other mice in the cage or from their own bodies. The internal ingestion of the camelid cream by the mice could indicate the possible benefits of camelid cream as a functional food.

After the first week, in the group treated as described with the camelid cream, 4 out of 5 mice responded positively with hair starting to grow. Health and hair growth continued to improve each week. After 4 weeks, the mice each weighed 25 gm with normal length of body from snout to the end of hip is 8 cm and the length of the tail is 8 cm (normal adult weight and size) with thick complete fur cover. The remaining mouse in this group responded to the treatment slowly but surely. In comparison, of the group that did not receive the treatment with camelid cream, 3 out of 5 mice were dead by age of 5 and 6 weeks. The remaining 2 mice remained severely growth retarded at approximately two-thirds normal size and by 8 weeks of age, with weight unchanged at 15 gm, were still demonstrating severe hair loss and stunted growth.

Example VI

Treatment of Different Types of Eczema

In another example, the composition of the present invention is useful in the treatment of different types of eczema.
Methods—VI
In this example a child patient (9 years old) with atopic dermatitis on the back of the knees, a second child patient (12 years old) with acute dermatitis flexural eczema on inner arm and a male patient (27 years old) with acute dermatitis condition (chronic eczema) on thigh were treated topically with camelid fat cream to create a thin film of fat on the skin.
Results—VI
The child patient (9 years old) with atopic dermatitis on the back of the knees was treated twice daily for 2 weeks, then tapered to once daily, and then maintained at one application on alternative days. The cream was applied at night and in the morning for 2 weeks resulting in no infection, pain relief and re-growth of normal skin. Then the treatment tapered to once daily for 1 week then maintained at once on alternative days for 1 week.

The child patient (12 years old) with acute dermatitis flexural eczema on the inner arm was treated twice daily for 2 weeks, and then tapered to once daily and finally maintained at once on alternative days, resulting in a reduction of the inflammation associated with eczema.

The male patient (27 years old) with acute dermatitis condition (chronic eczema) on thigh was treated twice daily for 2 weeks, and then tapered to once daily and maintained at once on alternative days and the inflammation associated with the eczema was reduced.

While not wishing to be bound by theory, the example suggests the camelid fat cream may be useful in treatment of acute dermatitis in humans.

Example VII

Treatment of Seborrhoeic Dermatitis

In this example a male patient (19 years old) with seborrhoeic dermatitis on the back was treated topically with camelid fat cream to create a thin film of fat on the skin.
Method—VII
The cream was applied at night and in the morning for 2 weeks resulting in no infection, pain relief and re-growth of normal skin. Then the treatment tapered to once daily for 1 week then maintained to once on alternative days for 1 week.

While not wishing to be bound by theory, the example suggests the camelid fat cream may be useful in treatment of seborrhoiec dermatitis in humans.
Discussions VI & VII
Accordingly, the compositions of the present invention may be used in a variety of treatments, including treatments of all types of eczema.

Example VIII

Treatment of Leathery and Dry Skin on Elbows

In another example, the composition of the present invention is useful in the treatment of leathery and dry skin on elbows.
Methods—VIII
In this example a man (60 years old) with leathery and dry skin on elbows. The nude right elbow was treated topically with camelid fat cream to create a thin film of fat and the left elbow was not treated as a control. The cream was applied at night and in the morning.
Results—VIII
After only 2 days the treatment resulted with a re-growth of normal skin on the right elbow in comparison to the untreated left elbow. The procedure was repeated on a second male subject with more extensive leathery skin patches on both elbows where the patches became soft and pliable after the first application with a lightening of the colour following each further treatment.

Example IX

Treatment of Lessened Blood Flow in Tissues

From the above-noted Example III for "Treatment of Age Spots", we noticed that the camelid cream appears to increase blood flow particularly in the large veins to the application site within 30 seconds of application and lasting more than 6 hours.
Method—IX
The camelid cream was applied topically to human skin, including the area around the male genitalia.
Results—IX
Bulging veins at the application site are visible immediately after application and lasting for several hours.

Example X

Treatment of Loosened Skin and Wrinkles

A wrinkle, also known as a rhytide, is a fold, ridge or crease in the skin. Skin wrinkles typically appear as a result of aging processes such as glycation, habitual sleeping positions, loss of body mass, or temporarily, as the result of prolonged immersion in water. Age wrinkling in the skin is promoted by habitual facial expressions, aging, sun damage, smoking, poor hydration, excess alcohol consumption and various other factors.

Method—X

Camelid cream was applied for the purposes of skin tightening and to prevent wrinkling.

In the right hand which was treated with the camelid cream twice daily for 3 weeks, the wrinkles were reduced, the skin was lighter, dry skin was moisturized and healthy-looking. The improved skin texture remained even on days where there was no application of cream and reduction of rough, dry skin had a lasting result on areas treated.

Results—X

After 3 weeks of treatment by the topical application, the camelid cream appears to reverse skin aging, where wrinkles are reduced; skin is lightened and dry skin is moisturized, leaving skin naturally healthy-looking.

Example XI

Treatment of Athlete's Foot

Athlete's foot, also known as "ringworm of the foot" and *tinea pedis* is a fungal infection of the skin that causes scaling, flaking, and itching in affected areas. Although the condition typically affects the feet, it can spread to other areas of the body, including the groin. About 70% of the population in the world is believed to experience a cutaneous mycotic infection at some point in their lives. Athlete's foot, the most prevalent mycotic infection worldwide, is caused by a Dermatophytes mold the *Trichophyton* sp.

Method—XI

A male patient (44 years old) who had developed Athlete's foot or *tinea pedis* on both feet was treated topically with about 1 gram of camelid fat cream on each foot to create a thick film of fat on the nude skin. The cream was applied day and night and washed in the morning, then repeated daily for 4 weeks.

Results—XI

Following the first application, the itching in affected areas stopped and after 2 weeks the bleeding, scaling, flaking of skin no longer occurred. After 4 weeks the infection was reduced, along with pain relief and slow re-growth of normal skin. Then the treatment tapered to once daily at night.

Example XIII

Treatment of Itchiness from Mosquito Bites and Pain from Bee Stings

Results XIII

Following the topical application of the camelid cream, a reduction in the itch from mosquito bites and the pain from bee stings was observed 15 minutes after the treatment had been administered.

CONCLUSIONS

The results herein suggest that when human skin is treated with camelid fat cream, the blood flow improves within 30 seconds and the increased flow lasts more than 6 hours. The increased blood flow enriches the tissues with all important growth factors for cells and tissues, qualities tied to skin aging, reducing wrinkles, lighter skin pigmentation, relieving dry skin and leaving the treatment site naturally healthy-looking.

The camelid hump fat may be used as a novel drug delivery mechanism to tissues since after a drug enters the systemic circulation, it is distributed to the body's tissues. Distribution is generally uneven because of differences in blood perfusion, tissue binding (eg. because of lipid content), regional pH, and permeability of cell membranes.

The entry rate of a drug into a tissue depends on the rate of blood flow to the tissue, tissue mass and partition characteristics between blood and tissue. Distribution equilibrium (when entry and exit rates are the same) between blood and tissue is reached more rapidly in richly vascularized areas, unless diffusion across cell membranes is the rate-limiting step. After equilibrium, drug concentrations in tissues and in extracellular fluids are reflected by the plasma concentration. Metabolism and excretion occur simultaneously with distribution, making the process dynamic and complex.

For interstitial fluids of most tissues, drug distribution rate is determined primarily by perfusion. For poorly perfused tissues (eg, muscle, fat), distribution is very slow, especially if the tissue has a high affinity for the drug. The camelid cream can be used as an alternative to steroids for increasing oxygen levels and blood flow in tissues.

Moreover, the camelid cream may also help to treat skin conditions associated with obesity which is implicated in a wide spectrum of dermatologic diseases, including acanthosis nigricans, acrochordons, keratosis pilaris, hyperandrogenism and hirsutism, striae distensae, adiposis dolorosa, and fat redistribution, lymphedema, chronic venous insufficiency, plantar hyperkeratosis, cellulitis, skin infections, hidradenitis suppurativa, psoriasis, insulin resistance syndrome, and tophaceous gout.

Topical application of the camelid cream has also been found to relieve the itchiness of mosquito bites and the pain from bee stings 15 minutes after the treatment has been administered.

All publications, patents and patent applications mentioned in this Specification are indicative of the level of skill those skilled in the art to which this invention pertains and are herein incorporated by reference to the same extent as if each individual publication patent or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

REFERENCES

Chatelain E and Gabard B (2001) Photostabilization of Butyl methoxydibenzoylmethane (Avobenzone) and Ethylhexyl methoxycinnamate by Bis-ethylhexyloxyphenol methoxyphenyl triazine (Tinosorb S), a new UV broadband filter. Photochem Photobiol 74 (3):401-6.

Ching K (2008) Enzymatic production of feruloylated acylglycerols from olive fatty acid distillates as sunscreen agents. Masters thesis, Universiti Putra Malaysia.

Clancy S (2008) DNA damage & repair: mechanisms for maintaining DNA integrity. Nature Education 1(1).

Gunstone F D and Russell W C (1954) Animal fats: 4. The component acids of crocodile fat. Biochem J. 57(3): 462-465.

Haasmann S O (1998). Analytical characterization of camel meat and milk fat. A thesis submitted for the degree of Doctor of Philosophy. Department of Chemistry, Brunel University.

Stephens T J, Herndon J H, Colon L E and Gottschalk R W (2011) The impact of natural sunlight exposure on the UVB-sun protection factor (UVB-SPF) and UVA protection factor (UVA-PF) of a UVA/UVB SPF 50 sunscreen. J Drugs Dermatol 10(2):150-155.

Tortora G J and Derrickson B (2012) The cardiovascular system: The Blood. In: Principles of Anatomy and Physiology, 13th. John Wiley and Sons, Inc. 729-732.

What is claimed is:

1. A method for the treatment of a subject in need thereof, comprising topically administering camel hump fat to the subject, wherein the subject has melanoma.

2. The method as in claim 1 wherein the camel hump fat is prepared by (i) heating a portion of fat from a camel hump and (ii) removing a proteinaceous connective tissue from the heated camel hump fat, thereby providing a camel hump fat cream.

3. The method as in claim 2, wherein the portion of camel hump fat is heated at about 60° for about 45 minutes.

4. The method as in claim 2, wherein the portion of camel hump fat is heated at about 100° for about 20 minutes.

5. A method for treating a melanoma in a subject in need thereof, the method comprising:
    heating camel hump fat to liquefy the camel hump fat;
    filtering the heated camel hump fat to remove a proteinaceous connective tissue of the camel hump fat;
    allowing the camel hump fat to cool; and
    applying the camel hump fat topically to the melanoma.

* * * * *

UNITED STATES PATENT AND TRADEMARK OFFICE
CERTIFICATE OF CORRECTION

PATENT NO. : 10,335,438 B2
APPLICATION NO. : 14/773382
DATED : July 2, 2019
INVENTOR(S) : Sabah Abdul Amer Jassim, Atheer Abdulrazzaq Al Doori and Richard George Limoges Page 1 of 1

It is certified that error appears in the above-identified patent and that said Letters Patent is hereby corrected as shown below:

On the Title Page

Item (73) please add:
Assignee: Camoleum Inc., Windsor, Ontario, (CA)

Signed and Sealed this
Twenty-first Day of April, 2020

Andrei Iancu
*Director of the United States Patent and Trademark Office*